United States Patent [19]

Hasegawa et al.

[11] 3,932,030
[45] Jan. 13, 1976

[54] ILLUMINATING DEVICE IN AN OPHTHALMOMETER

[75] Inventors: Hiroshi Hasegawa, Kawasaki; Toru Sato, Tokyo, both of Japan

[73] Assignee: Nippon Kogaku K.K., Tokyo, Japan

[22] Filed: May 16, 1974

[21] Appl. No.: 470,561

[30] Foreign Application Priority Data
May 22, 1973 Japan.......................... 48-59456[U]

[52] U.S. Cl........................................ 351/6; 351/13
[51] Int. Cl.².......................................... A61B 3/00
[58] Field of Search.................. 351/6, 7, 13, 15, 16

[56] References Cited
UNITED STATES PATENTS
2,902,899  9/1959  Cuppers et al.......................... 351/6
3,542,458  11/1970  Volk..................................... 351/39

Primary Examiner—Nathan Kaufman
Attorney, Agent, or Firm—Fitzpatrick, Cella, Harper & Scinto

[57] ABSTRACT

In an ophthalmometer comprising a chart plate, an illuminating device for illuminating the chart plate, a viewing optical system having an optical measurement adjust member for viewing therethrough the chart image projected by the illuminating device upon the cornea of an eye to be examined, a scale read-out device movable with the optical member and having a cornea curvature radius scale plate, and an astigmatism axis angle scale plate, the illuminating device comprises a chart illuminating light source member disposed behind the chart and within the viewing optical system and being in an annular form corresponding to the configuration of the chart of the chart plate. The illuminating device further includes a reflector member having light-transmitting portions for directing therethrough light beams for illuminating the two scale plates, respectively.

2 Claims, 3 Drawing Figures

ILLUMINATING DEVICE IN AN OPHTHALMOMETER

BACKGROUND OF THE INVENTION

1. Field of the Invention

This invention relates to an illuminating device in an ophthalmometer which is a measuring device for measuring the curvature radius of the cornea of an eye, the astigmatism of the cornea, etc.

2. Description of the Prior Art

There are various types of the ophthalmometer. By the operating method involved during measurement, they may generally be classified into the Javal-Schiötz type wherein measurement is effected by moving a chart projected upon the cornea or the like and the Sutcliffe or the Littmann type wherein measurement is effected by operating an optical member within a viewing optical system.

The present invention pertains to the ophthalmometer of the latter type and the conventional ophthalmometer of such type will hereinafter be described with respect, for example, to the Sutcliffe type ophthalmometer.

Referring to FIG. 1 of the accompanying drawings, there is shown the Sutcliffe type ophthalmometer according to the prior art. A chart image projected upon the cornea of an eye 1 to be examined may be provided by an illuminating light passed from a light source 2 disposed laterally of a viewing optical system and directed through a diffuser plate 3 and via a mirror 4 obliquely disposed on the optical axis T, to illuminate a chart plate 5. The chart image projected upon the cornea of the eye 1 to be examined may be viewed by the viewing optical system comprising an objective 6 and an eye-piece 7, through light-transmitting portions formed centrally of the chart plate 5 and of the mirror 4.

As the chart image is being so viewed, the curvature radius of the cornea of the eye 1 may be measured by operating an optical measurement adjust member 8 (which comprises two prisms for measuring two principal radial lines of the cornea astigmatism, respectively, the prisms being movable along the optical axis T to measure the curvature radius or like factor of the cornea).

In the conventional ophthalmometer of the described type, however, the light source means for illuminating the chart is projectedly disposed laterally outwardly of the viewing optical system and the mirror for directing the light from the source to the chart is obliquely disposed between the objective and the chart plate, and this has led to a larger size of the entire device which is particularly undesirable as an ophthalmometer wherein various operations occur with the viewing optical system being looked into.

SUMMARY OF THE INVENTION

The present invention has, for its object, to solve the above-noted problems and to provide an illuminating device which is adapted to be effectively utilized for the illumination of the chart as well as for the illumination of other items.

To achieve the above object, the ophthalmometer of the present invention comprises a chart plate, an illuminating device for illuminating the chart plate, a viewing optical system having an optical measurement adjust member for viewing therethrough the chart image projected by the illuminating device upon the cornea of an eye to be examined, a scale read-out device movable with the optical measurement adjust member and having a cornea curvature radius scale plate for indicating the value of the cornea curvature radius, and a scale plate for indicating the angle of astigmatism axis. The illuminating device may comprise a chart illuminating light source disposed behind the chart plate and within the viewing optical system and being in an annular form corresponding to the chart of the chart plate. The illuminating device may further include a reflector member disposed at that side of the light source opposite to the chart plate for condensing the light beam from the light source onto the chart of the chart plate. The reflector member has light-transmitting portions for directing therethrough light beams for illuminating the cornea curvature radius scale plate and the astigmatism axis angle scale plate, respectively.

The invention will become more fully apparent from the following detailed description thereof taken in conjunction with the accompanying drawings.

DESCRIPTION OF THE PREFERRED EMBODIMENTS

Figure 2:
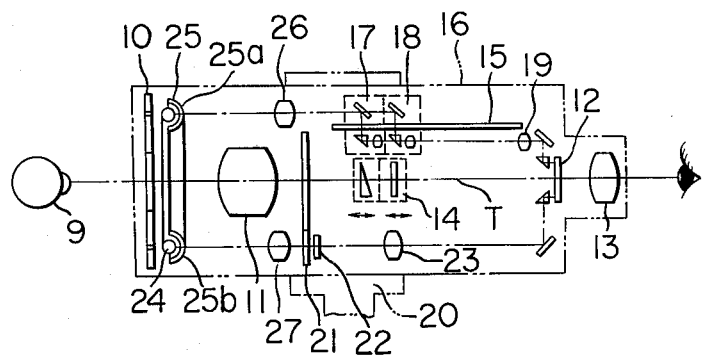
FIG. 2 is a schematic view illustrating an embodiment of the present invention.
Figure 3:
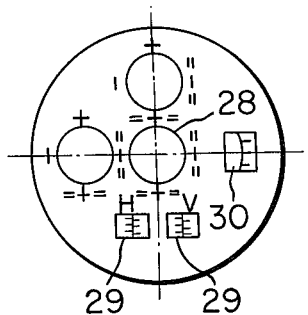
FIG. 3 shows the view field in the device of FIG. 2.

An embodiment of the present invention will hereinafter be described with respect, for example, to the Sutcliffe type ophthalmometer as shown in FIGS. 2 and 3.

Figure 1:
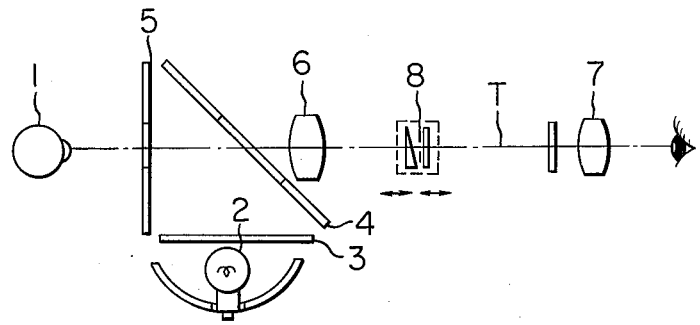
FIG. 1 is a schematic view illustrating the Sutcliffe type ophthalmometer according to the prior art.

In FIG. 2, there is seen an eye 9 to be examined, a chart plate 10 formed with a chart (see FIG. 3), an objective 11, a focusing plate 12, an eye-piece 13 and an optical measurement adjust member 14. This optical member is similar in construction to that of FIG. 1. These elements 11, 12, 13, and 14 together constitute a viewing optical system.

A scale plate 15 for indicating the values of the cornea curvature radii of two principal radial lines of cornea astigmatism is fixedly secured to a viewing optical system housing 16. Optical members 17 and 18 are movable with respective prisms of the optical measurement adjust member 14 and cooperate with an image forming lens 19 to form, on the focusing plate 12, the image of the divisions in the scale plate 15 representing the cornea curvature radii. These elements 15, 17, 18 and 19 together constitute a scale read-out device similar to the conventional one for the cornea curvature radii. The viewing optical system housing 16 is mounted on a prop 20 on an unshown bed for rotation about the optical axis T. A scale plate 21 for indicating the angle of astigmatism axis is mounted integrally with the prop 20. There is further provided a view field frame 22, and a lens 23 for forming, on the focusing plate 12, the image of the astigmatism axis angle scale plate 21. A light source 24 for illuminating the chart is in an annular form corresponding to the configuration of the chart on the chart plate 10. A reflector member 25 forming the body of an illuminating device is in an annular form similar to the light source 24. These elements 24 and 25 together constitute an illuminating device. The reflector member 25 is formed with light-transmitting portions 25a and 25b toward said scale plates 15 and 21 to illuminate them. Illuminating optical system 26 and 27 are provided for causing the illuminating light from the light source 24 to be projected upon the different scale plates 15 and 21, respectively.

Thus, the chart image projected by the annular illuminating device upon the cornea of the eye 9 to be examined is passed through the objective 11 and the optical measurement adjust member 14 and focused on the focusing plate 12 and may be viewed through the eye-piece.

On the other hand, the scale plates 15 and 21 are respectively illuminated by the beams of illuminating light passed through the light-transmitting portions 25a and 25b of the reflector member 25, and the images of the divisions in the respective scale plates are formed on the focusing plate 12 with the aid of the optical systems 18, 19, 23 and may be read out within the view field through the eye-piece 13 (see FIG. 3).

In the view field shown in FIG. 3, the chart image is designated by 28, the scale image representing the cornea curvature radius is designated by 29 and the scale image representing the angle of astigmatism axis is designated by 30.

Thus, the measurement of the cornea curvature radius or the like may be accomplished through conventional operations.

With the above-described construction of the present invention, the light source for illuminating the chart is in the form of an annular illuminating device corresponding to the configuration of the chart and such annular illuminating device is disposed behind the chart plate and in the space within the viewing optical system housing, and this leads to a more compactness and greatly improved operability of the entire device as compared with the conventional ophthalmometer of this type. Moreover, the fact that the chart illuminating light source is disposed in the described manner is highly useful inasmuch as the light for illuminating the various view-field reading scales disposed around the viewing optical system can easily be derived from the annular illuminating device corresponding in arrangement to the view-field reading scales.

We claim:

1. An ophthalmometer in which a chart plate is projected on the cornea of an eye to be examined, and by the image reflected thereby the curvature radius of the cornea of an eye and the angle of astigmatism axis are measured, comprising an optical system (11, 12, 13) for viewing the chart image reflected by the cornea, a light source (24) formed to surround the optical path of the viewing optical system for projecting the chart plate onto the cornea, displaceable measuring means (14, 20) for measuring the curvature radius of the cornea and the astigmatism axis, scale means (15, 21) for indicating each amount of displacement of the measuring means as the curvature radius and the angle of rotation, and means (25, 25a, 25b, 26, 27, 17, 18) for dividing light from the light source and illuminating the scale means.

2. An ophthalmometer according to claim 1, wherein said viewing optical system includes a focusing plate for forming the image of said chart plate and an image forming optical system for forming the image of said scale means on the focusing plate.

* * * * *